United States Patent [19]
Huebner

[11] Patent Number: 5,601,565
[45] Date of Patent: Feb. 11, 1997

[54] OSTEOTOMY METHOD AND APPARATUS

[76] Inventor: Randall J. Huebner, 18560 SW. Hart Rd., Aloha, Oreg. 97005

[21] Appl. No.: 459,516

[22] Filed: Jun. 2, 1995

[51] Int. Cl.⁶ .............................. A61F 5/00; A61B 17/58
[52] U.S. Cl. .................. 606/87; 606/79; 606/88; 606/89
[58] Field of Search ................... 606/79, 82, 87, 606/88, 89

[56]     References Cited

U.S. PATENT DOCUMENTS

| | | |
|---|---|---|
| 4,349,018 | 9/1982 | Chambers . |
| 4,409,973 | 10/1983 | Neufeld . |
| 4,421,112 | 12/1983 | Mains et al. . |
| 4,501,266 | 2/1985 | McDaniel . |
| 4,509,511 | 5/1985 | Neufeld . |
| 4,565,191 | 12/1986 | Slocum . |
| 4,627,425 | 12/1986 | Reese . |
| 4,703,751 | 11/1987 | Pohl . |
| 4,708,133 | 11/1987 | Comparetto . |
| 4,750,481 | 6/1988 | Reese . |
| 4,773,407 | 9/1988 | Petersen ................................... 606/88 |
| 4,907,578 | 3/1990 | Petersen . |
| 4,938,230 | 7/1990 | Machek et al. . |
| 4,952,214 | 8/1990 | Comparetto . |
| 5,035,698 | 7/1991 | Comparetto . |
| 5,049,149 | 9/1991 | Schmidt . |
| 5,112,334 | 5/1992 | Alchermes et al. . |
| 5,116,338 | 5/1992 | Poggie et al. ............................. 606/90 |
| 5,147,364 | 9/1992 | Comparetto . |
| 5,213,112 | 5/1993 | Niwa et al. . |
| 5,246,444 | 9/1993 | Schreiber . |
| 5,364,401 | 11/1994 | Ferrante et al. .......................... 606/79 |
| 5,376,093 | 12/1994 | Newman .................................. 606/88 |
| 5,431,653 | 7/1995 | Callaway .................................. 606/90 |
| 5,468,244 | 11/1995 | Attfield et al. ........................... 606/90 |

*Primary Examiner*—Michael Powell Buiz
*Assistant Examiner*—Mark S. Leonardo
*Attorney, Agent, or Firm*—Kolisch, Hartwell, Dickinson, McCormack & Heuser

[57]     ABSTRACT

The present invention relates to an osteotomy guide with a saw guide and an alignment member to be mounted on a pivot pin at the apex of a wedge of bone to be removed. The saw guide establishes a cut plane and guides a cutting device as it cuts through the bone in the cut plane. The alignment member projects in a direction generally normal or transverse to the cut plane and provides a reference for the alignment steps in the osteotomy procedure as described below. The saw guide and alignment member are either permanently or selectively coupled to one another for common pivotal motion about the pivot pin. The present method of carrying out the osteotomy involves aligning the alignment member with a predetermined anatomical landmark and making a first cut. After the first cut is made the alignment member is pivoted about the pivot pin, together with the saw guide which is coupled to it, into alignment relative to a second anatomical landmark. By choosing appropriate landmarks, the saw guide will automatically be placed so that the angle between the cuts results in the proper correction.

23 Claims, 4 Drawing Sheets

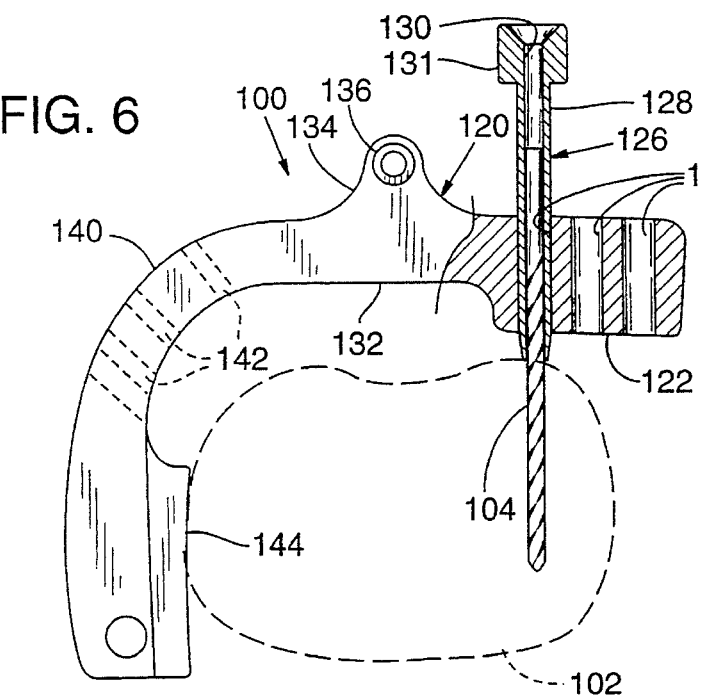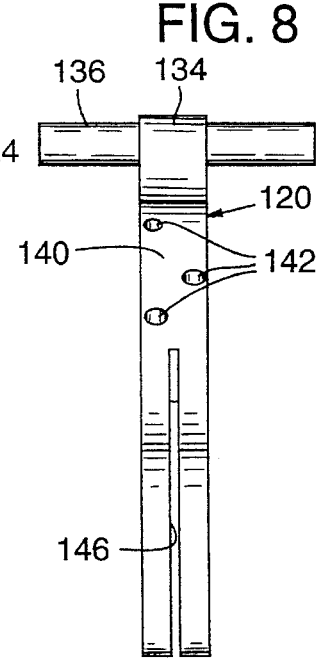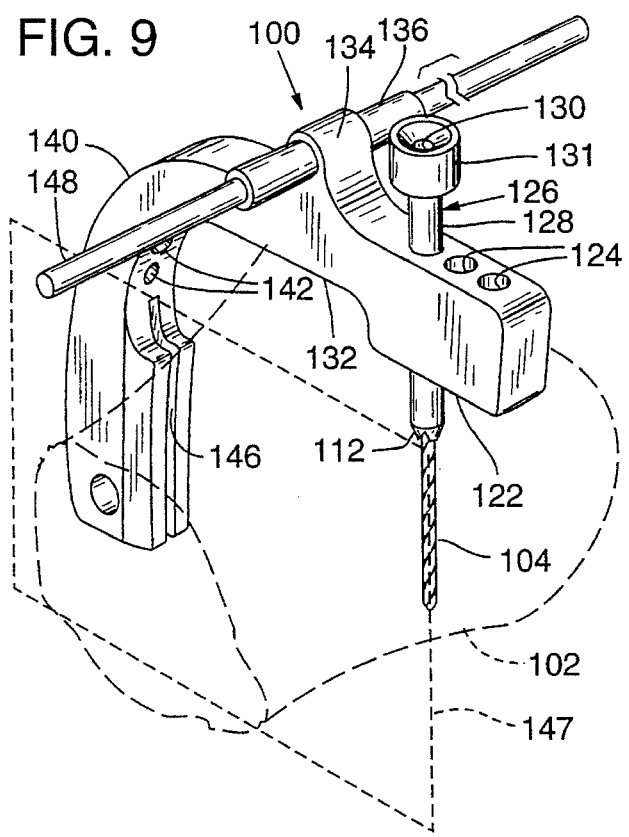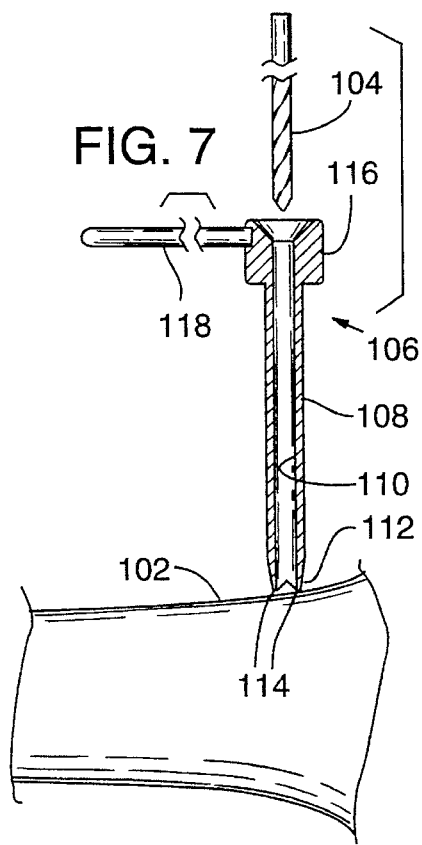

OSTEOTOMY METHOD AND APPARATUS

This invention relates generally to osteotomy guides to facilitate making cuts in a bone. More particularly, the invention relates to an improved method and apparatus for correcting deformities in a bone or joint by making a pair of intersecting, angularly-displaced cuts to excise a wedge-shaped piece of bone.

BACKGROUND

An osteotomy is a surgical procedure involving dividing or cutting a piece out of a bone to correct a bone or joint deformity. Such deformities may result from age, injury, birth defect and/or disease, such as arthritis. A particularly common deformity susceptible to treatment by osteotomy is a varus or valgus displacement of the knee joint, more commonly referred to as a knock-kneed or bow-legged condition, respectively. This condition can be corrected by a tibial osteotomy procedure. A second common type of deformity, frequently caused by overly tight shoes, involves a twisting in of the big toe toward the rest of the foot, known as a hallux valgus deformation. A hallux valgus deformity can frequently be successfully treated by a metatarsal osteotomy to realign the metatarsal.

Angular deformations, such as described above, can be corrected by one of two major osteotomy techniques. In the first of the techniques, the angular alignment of a bone is altered by making a cylindrical profile cut through the bone where the realignment is to be effected. The severed sections of a bone cut in this fashion can be pivoted relative to one another about the axis of the cylindrical cut, while maintaining substantially complete bone contact at the cut. The surgeon must position the bone sections in the desired alignment and stabilize the bone while it heals. Both the stabilization and the alignment can be problematic when this method is employed.

A second technique for correcting angular deformations involves the removal of a cuneiform or wedge-shaped section of bone extending substantially, but not completely, across the bone generally transverse to its long axis. By leaving a small amount of bone at the apex of the wedge, a hinge-like articulation is created, which stabilizes the bone as the gap, which results when the wedge is removed, is closed. By precisely controlling the wedge angle, the desired angular correction is reliably established. In the prior art, the desired angular correction is typically determined pre-operatively by measurements from X-rays of other imaging techniques, and in some cases, by simple visual estimation. The predetermined correction angle is used to set the guide, which is then used to make the cuts.

Several varieties of osteotomy guides for making cuneiform osteotomies are shown in the prior art. U.S. Pat. Nos. 4,627,425 and 4,750,481 to Reese disclose a system to make a second cut at a predetermined angle relative to a first cut. The system employs a flat follower pivotally connected to a saw guide. After making the first cut, the follower is set and secured at the desired predetermined angle relative to the guide and inserted into the first cut. By placing the follower in the first cut, the guide is automatically placed so that the second cut occurs at the desired predetermined angle relative to the first cut.

Numerous references, such as U.S. Pat. Nos. 4,349,018, 4,421,112, 4,565,191, 5,112,334 and 5,246,444, disclose devices that provide two angularly displaced guides, one for each cut, along which both cuts are made without repositioning the device. As with the guide and follower systems described above, such devices require that the surgeon predetermine the desired correction angle.

Either of the above described mechanisms for guiding the cuts at predetermined angles are generally able to accurately establish the cut locations once the wedge angle is set. The primary source of error in such systems thus becomes determining the angle at which to set the devices. Measurements from X-rays of the affected bone or bones are probably the most common method of determining the correction angle. Unfortunately, determining the correct angle from an X-ray is dependent on taking the X-ray from the proper angle relative to the bone or bones. Thus, in the case of the tibial osteotomy, if the patients leg is rotated slightly about its longitudinal axis, i.e., the foot turned in or out, the apparent angle between the tibia and femur may be altered. It is likewise apparent that visual estimation of the correction angle is subject to considerable error.

It is therefore an object of the present invention to provide an osteotomy guide with which it is not necessary to determine preoperatively the desired correction angle.

It is another object of the current invention to provide an osteotomy method in which the correction is automatically established during the osteotomy.

Yet another object of the current invention is to provide an osteotomy method in which the correction angle is determined during the surgery by reference to anatomical landmarks.

One more object of the present invention is to provide an osteotomy guide with a structure suitable for use in determining the correction angle for an osteotomy.

Another object of the present invention is to provide a simple, easy to use osteotomy guide and surgical technique that together result in a rapid and precise osteotomy.

SUMMARY OF THE INVENTION

The above objects are best realized by providing an osteotomy guide with a saw guide and an alignment member to be mounted on a pivot pin at the apex of a wedge of bone to be removed. The saw guide establishes a cut plane and guides a cutting device as it cuts through the bone in the cut plane. The alignment member projects in a direction generally normal or transverse to the cut plane and provides a reference for the alignment steps in the osteotomy procedure as described below. The saw guide and alignment member are either permanently or selectively coupled to one another for common pivotal motion about the pivot pin.

The present method of carrying out the osteotomy involves aligning the alignment member with a predetermined anatomical landmark and making a first cut. After the first cut is made the alignment member is pivoted about the pivot pin, together with the saw guide which is coupled to it, into alignment relative to a second anatomical landmark. By choosing an appropriate landmarks, the saw guide will automatically be placed so that the angle between the cuts results in the proper correction.

These and other advantages and features of the present invention will become apparent when consideration is given to the following detailed description and the accompanying drawings.

BRIEF DESCRIPTION OF THE DRAWINGS

FIG. 6 is a partial cutaway side view of another embodiment of an osteotomy guide assembly according to the present invention.

FIG. 7 shows how a drill guide is used to install a pivot pin for use in the invented osteotomy method.

FIG. 8 is an end view of the assembly of FIG. 6.

FIG. 9 is a perspective view of the assembly of FIG. 6 as mounted on a patient's tibia.

DETAILED DESCRIPTION OF THE PREFERRED EMBODIMENT

Figure 1A:
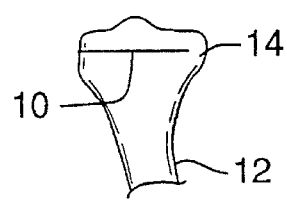
FIGS. 1a–c depict an osteotomy to remove a wedge-shaped piece of a bone.
Figure 1B:
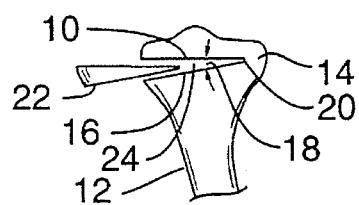
Figure 1C:

The steps involved in performing a cuneiform osteotomy are generally illustrated in FIGS. 1a–1c. As shown in FIG. 1a, first cut 10 is made in a bone 12 generally transverse to the long axis of the bone. First cut 10 extends substantially through the bone, leaving a portion of the bone intact to serve as a cortical hinge 14. A second cut 16 is made in bone 12 at an angle 18 relative to first cut 10. Angle 18 determines the angular correction yielded in the bone. The two cuts 10, 16 intersect at an apex 20 of a wedge-shaped piece 22 of bone 12. After cuts 10, 16 are made, wedge 22 is removed and bone 12 is bent at cortical hinge 14 to close the resultant gap 24.

Figure 2:
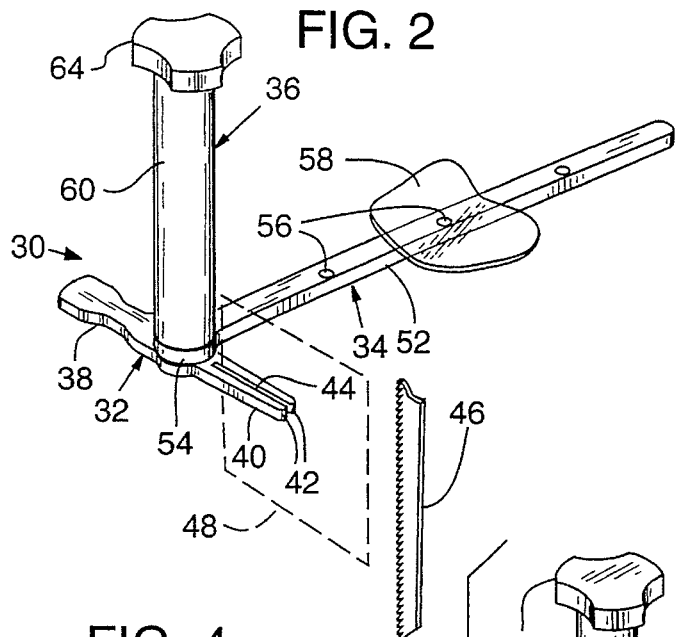
FIG. 2 is a perspective view of an osteotomy guide assembly according to the present invention.
Figure 3:
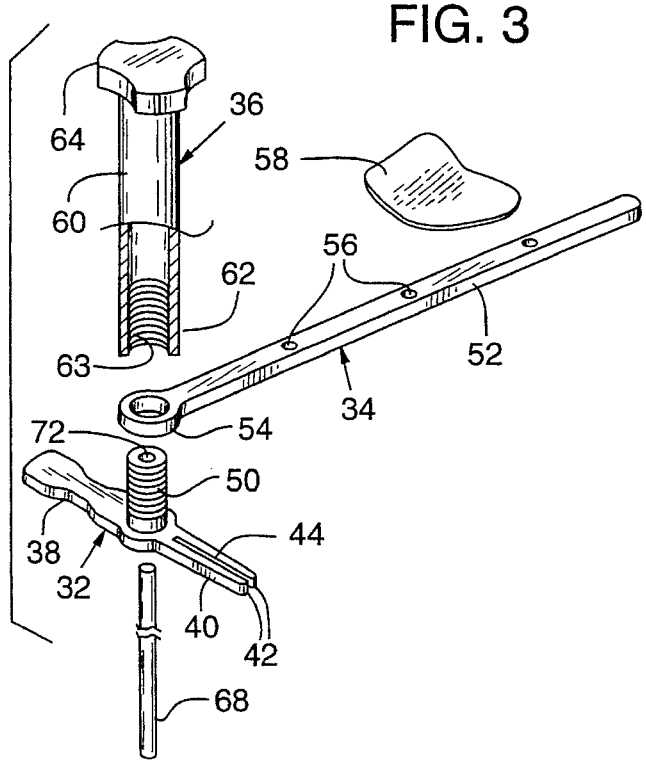
FIG. 3 is an exploded view of the assembly of FIG. 2.

A preferred embodiment of an osteotomy guide assembly according to the present invention particularly adapted for metatarsal osteotomies is illustrated generally at 30 in FIG. 2. Guide assembly 30 includes three major components: guide member 32, alignment member 34 and locking member 36. Guide member 32 has a generally elongate form and includes a handle portion 38 disposed toward one end and a saw guide 40 disposed toward the opposite end. Saw guide 40 is formed by two spaced-apart elongate fingers 42 separated by a planar slot 44 which is adapted to receive a saw blade 46. Saw blade 46, being slightly narrower than slot 44 can move freely up and down and back and forth therein, but is constrained to cut in a cut plane 48 established by slot 44. An elongate threaded stud 50 projects outwardly from guide member 32 between handle 38 and saw guide 40. See FIG. 3. The axis of stud 50 is generally perpendicular to the elongate axis of guide member 32 and parallel to cut plane 48 established by slot 44.

Alignment member 34 is made up of an elongate alignment bar 52 connected at one end to a circular collar 54 adapted to be placed over stud 50 and thereby pivotally connect alignment member 34 to guide member 32. Bar 52 includes a number of transverse locking holes 56 through which small pins or screws (not shown) can be installed to secure the bar to the bone while the cut is being made. A profile template 58, the use of which is described below, is slidably attached to move back and forth along the length of bar 52.

Locking member 36 has an elongate, generally cylindrical, central region 60 and a lower end 62 with an internally threaded cavity 63 for threaded engagement with stud 50. At the upper end of locking member 36 is a knob 64 to facilitate finger tightening of locking member 36 on stud 50. Until locking member 36 is tightened on stud 50 to clamp collar 54 between lower end 62 and guide member 32, alignment member 34 is free to pivot about stud 50 relative to saw guide 40. Tightening locking member 36 on stud 50 fixes the relative orientation of saw guide 40 and alignment member 34.

Figure 4:
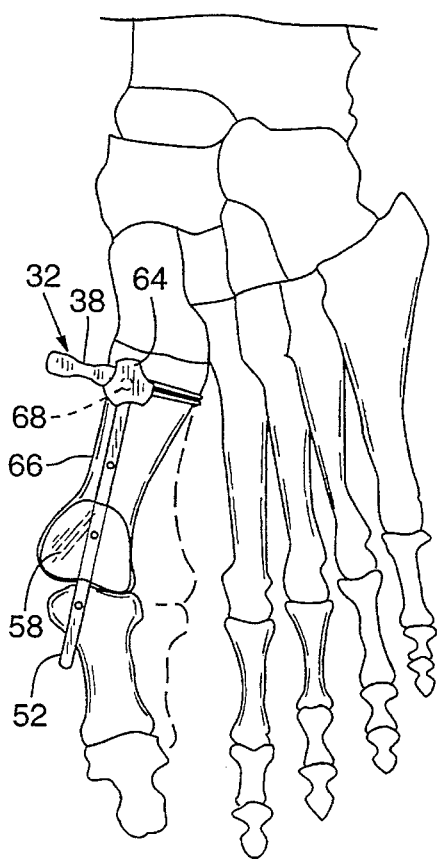
FIG. 4 shows the assembly of FIG. 2 mounted on a patient's foot.

Guide assembly 30 is pivotally mounted on a metatarsal 66 on a pivot pin 68. See FIGS. 4 and 5. During the operation, the surgeon chooses a location where a wedge of bone 70 from metatarsal 66 is to be removed to correct the deformity. The surgeon then drills a portion of pin 68 into the metatarsal at the apex of wedge 22. A pivot bore 72 extends axially through stud 50 and guide member 32 to fit over the portion of pin 68 projecting out of metatarsal 66. This allows guide assembly to pivot about pin 68 and results in the axis of pin 66 lying in the cut plane established by slot 44. The axis of pin 68, therefore, determines the plane in which the angular correction is effected, that plane being perpendicular to the axis of the pin. Pin 68 also serves as a stop to prevent saw blade 46 from cutting entirely through the bone. This is important because the narrow portion of bone left at the apex of wedge 22 serves as a hinge when the bone is bent to remove the deformity.

Figure 5:
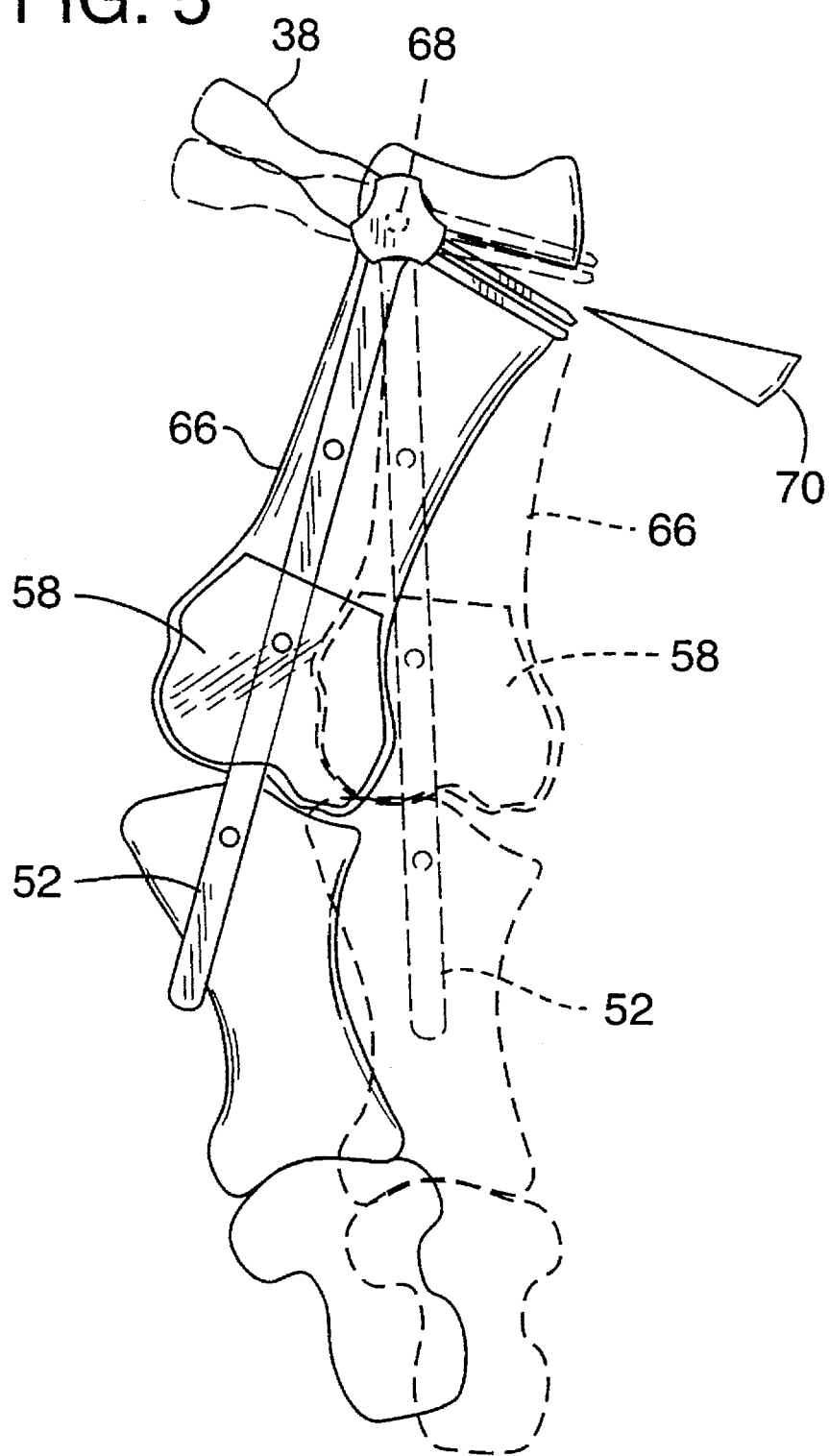
FIG. 5 illustrates the steps and corrective effect of the invented osteotomy method.

The use of guide assembly 30 in a metatarsal osteotomy is illustrated in FIG. 5. After guide assembly 30 is mounted on pin 68, alignment bar 52 and profile template 58 are adjusted so that profile template 58 lies over the distal end of metatarsal 66 as shown by the solid lines in FIG. 5. The outline of profile template 58 is adapted to closely match the outside profile of the distal end of metatarsal 66 to facilitate precise alignment of bar 52 with metatarsal 66. Once profile template 58 is properly placed, alignment bar 52 is secured to metatarsal 66 by placing one or more screws or pins through locking holes 56.

After alignment bar 52 is secured in place, the surgeon, using handle 38, pivots slot 44 into position at the desired location for the first cut. When slot 44 is properly located, locking member 36 is tightened, thereby fixing the orientation between alignment bar 52 and cut plane 48 established by slot 44. Slot 44 is then used to guide saw blade 46 as the first cut is made in the cut plane established by the slot. It should be noted that it is not critical that the orientation between alignment bar 52 and saw guide 40 be adjustable. Being able to choose the position of the first cut independent of the position of bar 52 merely allows the surgeon additional flexibility as to the orientation of the wedge relative to the longitudinal axis of the metatarsal. The important constraint is that the alignment between bar 52 and cut plane 48 established by saw guide 40 not change between the cuts.

In order to align slot 44 for the next cut, any pins or screws holding alignment bar 52 to metatarsal 66 are removed, thereby allowing guide assembly 30 to pivot freely on pin 68. The surgeon, without loosening locking member 36, pivots alignment bar 52 about pin 68 until profile template 58 lies over the desired final position of the distal end of metatarsal 66 as shown by the dashed lines in FIG. 5. The final position is chosen to set the correct spacing between metatarsal 66 and the adjacent metatarsal bone. Alignment bar 52 is then secured to metatarsal 66, and a second cut is made through slot 44 in cut plane 48 established thereby.

The two cuts sever wedge 70 from metatarsal 66. Wedge 70 is removed and metatarsal 66 is then bent to close the wedge-shaped gap left when wedge 70 was removed. Bone screws, staples or other types of fixation are applied to hold the gap closed while healing takes place.

Another embodiment of an osteotomy guide assembly according to the present invention is shown at 100 in FIG. 6. Guide assembly 100 is adapted to perform high tibial osteotomies and is pivotally mounted to the proximal end of a tibia 102 on a pivot pin 104.

As shown in FIG. 7 pivot pin 104 is installed on tibia 102 with the aid of a drill guide 106. Drill guide 106 insures that the pivot pin axis is perpendicular to the axis of tibia 102 and includes a cylindrical body 108 with an axial bore 110 and a lower end 112 with a number of grip points 114. A shoulder flange 116 is formed on body 108 on the end opposite lower end 112. An alignment rod 118 is fixed to shoulder flange 116 and extends radially and perpendicularly relative to the axis of bore 110.

The surgeon, after selecting the site for the osteotomy, places lower end 112 of drill guide 106 on tibia 102 at the apex of the wedge of bone to be removed. The action of grip points 114 against tibia 102 prevents lower end 112 from slipping on the surface of tibia 102 during subsequent alignment and drilling. In conjunction with the positioning of lower end 112, alignment rod 118 is adjusted to extend parallel to the longitudinal axis of tibia 102. The surgeon also tips body 108 so that the axis of bore 110 is perpendicular to the axis of flexion of the knee.

After drill guide 106 is properly aligned, pivot pin 104 is passed through bore 110 and drilled into tibia 102. About two inches of pivot pin 104 are left sticking out of tibia 102.

Guide assembly 100 further includes a guide member 120 as shown in FIGS. 6, 8 and 9. Guide member 120 includes a pivot end 122 through which are formed three pivot holes 124. Pivot holes 124 are adapted to fit over pivot pin 104 and are formed oversize to facilitate installation of member 120 on pin 104.

After member 120 is installed on tibia 102 and pivot pin 104, a pivot shim 126 is installed around pivot pin 104 and within one of pivot holes 124 to eliminate the play between the pin and the hole. Pivot shim 126 includes a cylindrical body 128 with an axial bore 130 and a shoulder flange 131 at one end. Shoulder flange 131 prevents shim 126 from passing entirely through hole 122. When installed, cylindrical body 128 fits through hole 122 and pin 104 passes through bore 130. The outside diameter of cylindrical body 128 should closely match the inside diameter of pivots holes 56 and, likewise, the diameters of pin 104 and bore 130 should be equal to each other. This eliminates any play in the pivotal joint between pin 104 and guide member 120.

Figure 10A:
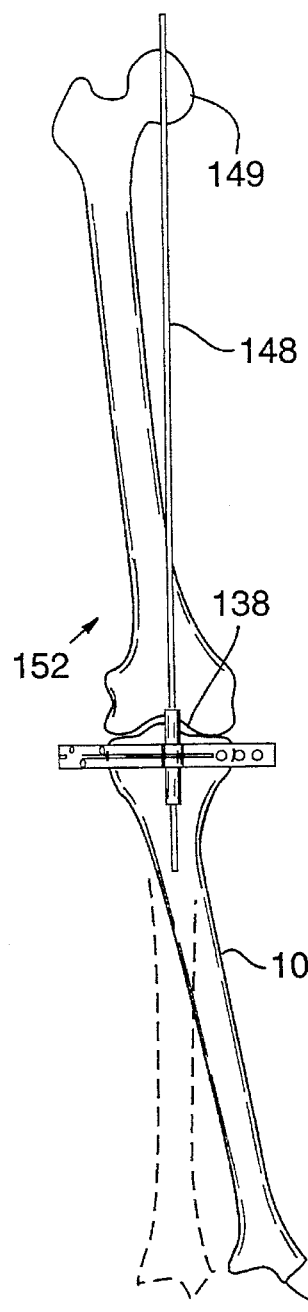
FIGS. 10a–c illustrate the tibial osteotomy process of the present invention.

Extending from pivot end 122 in a direction perpendicular to the axes of pivot holes 124 and across tibia 102 is an elongate cross arm 132. Arm 132 includes a raised portion 134 which holds an alignment tube 136. The axis of tube 136 is perpendicular to both the axis of the holes and the axis of arm 132. Raised portion 134 is positioned on arm 132 so that the axis of tube 136 lies directly over the medial compartment 138 of the knee. Provision of three pivot holes allows guide member 100 to accommodate various bone sizes while still maintaining this alignment. See FIG. 10a. Unless otherwise specified, references to positional relationships will be specified assuming a patient lying prone on their back with legs straight.

The end of arm 132 opposite pivot end 122 curves down around the side of tibia 102 forming an arcuate section 140. Arcuate section 140 includes three locking holes 142. The axes of locking holes 142 run generally radially from the axis of tibia 102. When guide member 120 is properly positioned for each cut, a number of fasteners in the form of pins or screws are driven through locking holes 142 to secure the guide member to the bone during the cut.

A saw guide portion 144 extends from the end of arcuate section 140 down along the side of tibia 102. A planar slot 146 bifurcates saw guide portion 144 along a plane intersecting the axis of pivot pin 104 and perpendicular to the axis of alignment tube 136. Slot 146 is adapted to receive and establish a cut plane 147 for a saw blade. The blade, which is not shown, can move back and forth through, and up and down in, slot 146, but is constrained to move and cut in the plane 147 of slot 146.

After guide member 120 is pivotally mounted on tibia 102, an alignment rod 148 is passed through alignment tube 136 for use in aligning the guide member for each cut. For the first cut, the free end of alignment rod 148 opposite tube 136 is positioned over the head 149 of the patient's femur. This automatically places saw guide 144 in position for the first cut. Under some circumstances, it may be beneficial to use an X-ray to establish the location of head 149. After securing guide member 120 to tibia 102, as described above, the surgeon makes the first cut in the cut plane established by saw guide 144.

Figure 10B:
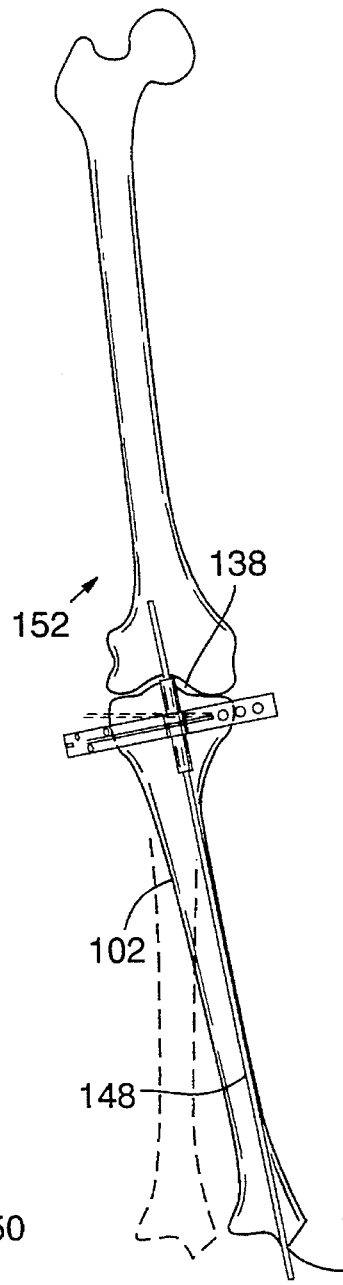

The position of the saw guide for the second cut is established by extending alignment rod 148 through tube 136 so that the free end is disposed toward the distal end of tibia 102. See FIG. 10b. The free end of alignment rod 148 is then aligned with the tip 150 of the distal end of tibia 102. Guide member 120 is again secured to tibia 102 and the second cut is made.

As with the metatarsal osteotomy procedure described above, the severed wedge of bone is removed and the bone is bent to close the gap. See FIG. 10c. Some form of stabilization is then applied to fix the bone portions in place during the healing process.

Figure 10C:
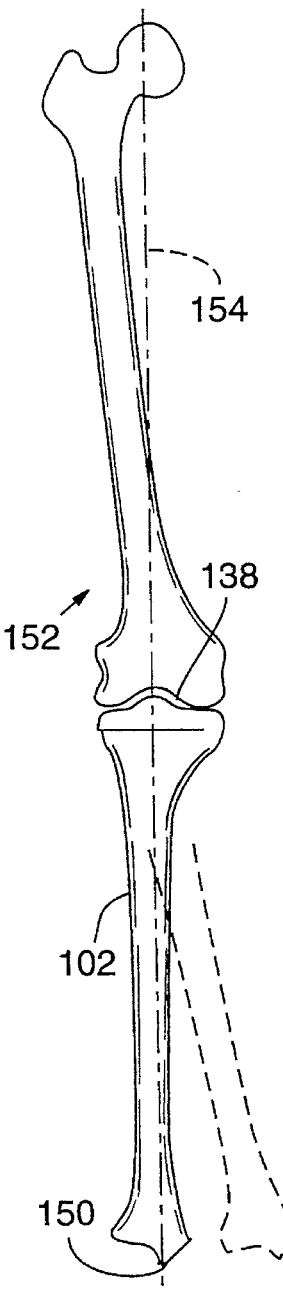

The correct alignment of a leg 152 is illustrated in FIG. 10c. It can be seen that a straight line 154, as viewed from above, extends from the center of head 149 of the femur, through medial compartment 138 of the knee to distal tip 150 of tibia 102. By referring to FIGS. 10a–c it will be seen that the above described process automatically establishes the proper correction angle to create this relationship. If one cut is made at a fixed angle relative to a line between head 149 of the femur and medial compartment 138, and the other cut is made at the same angle relative to a straight line between medial compartment 138 and distal tip 150 of tibia 102, the resultant alignment after the severed wedge is removed will be as shown in FIG. 10c.

The two described osteotomy methods have a common underlying approach of using anatomical landmarks for references to establish the relative angular position between the cuts. In the case of the metatarsal osteotomy, the first landmark is the distal end of the metatarsal. The second landmark is the desired final position of the distal end of the metatarsal, which is determined by reference to the adjacent metatarsal. For the tibial osteotomy, the first landmark is the head of the femur and the second landmark is the tip at the distal end of the tibia.

It will also be appreciated that the method for metatarsal osteotomies described above wherein the alignment member is set over current and desired final positions of some anatomical landmark could be used for tibial osteotomies. For example, the free end of alignment rod 148 could be aligned with the current position of the distal tip of the tibia for one cut and with the desired final position of the distal tip for the second cut.

It should be noted that the order of the cuts is irrelevant to achieving the correct final alignment. Nor is it necessary that the cut plane be perpendicular to the alignment tube and rod. Also, while not preferred, it is possible to carry out the present method with a guide assembly having two separate saw guides, and perhaps separate associated alignment members, pivotally connected to the pivot pin.

For guide assemblies, such as guide assembly 30 for metatarsal osteotomies, in which the orientation between the saw guide and the alignment member can be adjusted, it is not critical that the alignment member be aligned prior to the first cut. Rather, a first configuration must simply be established at some point wherein the alignment member is aligned with the first preselected landmark and the saw guide is positioned at the location of the first cut. It is the relative orientation between the saw guide and the alignment member in the first configuration that is of particular importance. The first cut is made in conjunction with this first configuration such that the saw guide is positioned at the location of the first cut, but indifferent to the relative orientation to the alignment member.

Thus, there are at least two distinct possibilities for how the first cut can be made in conjunction with the step of establishing a first configuration. First, the saw guide can be positioned for the first cut without reference to the alignment of the alignment member. In this case, the first cut is made and the alignment member, with the saw guide still in position for the cut, is afterward aligned with the first anatomical landmark to thereby establish the first configuration. At this point the orientation between the saw guide and the alignment member is preserved by locking the two together with the locking member, thereby preserving the proper relative orientation.

In the second alternative, the alignment member is aligned with the first anatomical landmark and locked to the saw guide, as positioned for the first cut, prior to making the cut. This allows the position of the saw guide to be stabilized by locking the alignment member to the bone, as described above in the context of metatarsal osteotomies.

In either case it is the relative orientation between the saw guide and the alignment member created when the alignment member is aligned with the first anatomical landmark and the saw guide is positioned for the first cut that is duplicated to place the second cut. The location of the second cut is automatically established by aligning the alignment member with the second anatomical landmark while maintaining or recreating the orientation between the alignment member and the saw guide determined in the first configuration. Typically, as in the preferred embodiment, the saw guide and alignment member are pivoted in unison after being locked together. However, the method of maintaining or reestablishing the proper relative orientation is not critical to the practice of the invention and there are many suitable ways in which the desired result could be accomplished.

By using anatomical landmarks, many of the sources of error in prior art methods are eliminated. For instance, when relying on X-rays to establish a correction angle, it is critical that the X-ray be taken from the proper angle with the patient's leg not being rotated. If the angle is incorrect or the patient's leg is rotated, the X-ray will give a false indication of the degree of correction required. It is frequently necessary to take quite a number of X-rays to establish an accurate correction angle. Simple visual estimation of the correction angle is likewise subject to considerable error. The present methods, in contrast, by making direct reference to anatomical landmarks intra-operatively, give the surgeon full control over the position of the patient's leg during the various steps and eliminate all of the guess work from the surgery.

The osteotomy methods and apparatus described above allow the surgeon to establish the amount of angular correction to be effected intra-operatively and without reference to X-rays or other imaging techniques. Use of the described apparatus and methods results in an osteotomy procedure that is faster and simpler, as well as more reliable, than the prior art osteotomy techniques.

It will now be clear that an improvement in this art has been provided which accomplishes the objectives heretofore set forth. While the invention has been disclosed in its preferred form, it is to be understood that the specific embodiment thereof as disclosed and illustrated herein is not to be considered in a limited sense as there may be other forms or modifications which should also be construed to come within the scope of the appended claims.

What is claimed is:

1. A method of performing an osteotomy to excise a wedge-shaped piece of a bone by making first and second angularly-displaced generally planar cuts, the method comprising:

providing a saw guide and an elongate alignment member coupled to the saw guide, where the saw guide establishes a cut plane and the elongate axis of the alignment member projects generally transversely out from the cut plane;

pivotally mounting the saw guide on the bone;

establishing a first configuration where the alignment member is aligned with a first preselected anatomical landmark and where the saw guide is positioned so that the cut plane established by the saw guide matches the plane of the first cut;

in conjunction with the step of establishing, making a first cut with the saw guide positioned so that the cut plane established by the saw guide matches the plane of the first cut;

pivoting the saw guide and the alignment member so that the alignment member is aligned with a second preselected anatomical landmark and the orientation between the saw guide and the alignment member is the same as in the first configuration; and making a second cut in the bone in the cut plane established by the saw guide as it is positioned in the step of pivoting.

2. The method of claim 1 where the bone is the tibia and further comprising the step of choosing the head of the femur as one of the anatomical landmarks and the distal tip of the tibia as the other anatomical landmark.

3. The method of claim 1 where the bone is a first metatarsal and further comprising the step of choosing the distal end of the metatarsal as one of the anatomical landmarks and the desired final position of the distal end of the metatarsal as the other anatomical landmark.

4. The method of claim 3 further comprising the step of providing a profile template slidably connected to the alignment member to move back and forth along the elongate axis thereof, where the outline of the profile template generally conforms to at least a portion of the distal end of the metatarsal and the step of establishing includes positioning the template over the first anatomical landmark.

5. The method of claim 1 further comprising the step of temporarily securing the saw guide to the bone so that it does not pivot relative thereto during the step of cutting.

6. The method of claim 5 further comprising the step of providing a saw guide including a planar slot adapted to guide a saw blade in the cut plane established by the saw guide.

7. The method of claim 6 further comprising the step of installing a pivot pin approximately at apex of the wedge-shaped piece of bone to be excised and wherein the saw guide and the alignment member are pivotally mounted to the pivot pin.

8. The method of claim 1 wherein the saw guide and the alignment member are pivotally connected and the pivotal orientation between the saw guide and the alignment member is selectively fixable and further including the step of locking the pivotal orientation between the saw guide and the alignment member prior to the step of pivoting.

9. An osteotomy method for removing a wedge-shaped piece of an elongate bone, the method comprising:
   installing a pivot pin at the approximate intersection of two angularly-displaced generally planar cuts to be made in the bone on opposite sides of the wedge, the axis of the pin being substantially parallel with the plane of both cuts;
   providing an osteotomy guide with a saw guide suitable for establishing a cut plane and an elongate alignment member extending generally transversely of the cut plane established by the saw guide;
   coupling the osteotomy guide to the pivot pin;
   aligning the alignment member with a predetermined portion of the bone;
   making a first cut in the bone along the cut plane established by the saw guide;
   pivoting the osteotomy guide about the axis of the pin to align the alignment member with the desired final position of the predetermined portion of the bone, where orientation between the cut plane and the alignment member is substantially the same before and after pivoting;
   cutting the bone along the cut plane established by the saw guide; and
   removing the wedge of bone.

10. The method of claim 9 further comprising the step of selecting the distal end of a metatarsal as the predetermined portion of the bone.

11. The method of claim 9 further comprising the step of fixing the orientation of the alignment member relative to the saw guide prior to the step of pivoting.

12. The method of claim 9 further comprising the steps of pivoting the saw guide to a desired position for the first cut followed by the step of fixing the orientation of the alignment member relative to the saw guide, where both steps occur prior to the step of making the first cut.

13. An osteotomy method for removing a wedge-shaped piece of bone from the proximal region of a patients tibia to make varus to valgus and valgus to varus corrections of the patient's knee joint, the method comprising:
   installing a pivot pin at the approximate intersection of two angularly-displaced generally planar cuts to be made in the tibia on opposite sides of the wedge;
   providing an osteotomy guide with a saw guide suitable for establishing a cut plane and an elongate alignment member extending generally transversely of the cut plane established by the saw guide;
   attaching the osteotomy guide to the pin so that the saw guide and the alignment member can pivot about the axis of the pin;
   aligning the saw guide and the alignment member so that the elongate axis of the alignment member is generally parallel to a line leading from the head of the patient's femur to the medial compartment of the knee joint;
   making a cut along the cut plane established by the saw guide;
   pivoting the saw guide and the alignment member so that the elongate axis of the alignment member is generally parallel to a line leading from the medial compartment the knee joint to the distal tip of the tibia and the orientation between the cut plane established by the saw guide and the elongate axis of the alignment member is the same as during the step of making a cut; and
   cutting the bone along the cut plane established by the saw guide as positioned in the step of pivoting.

14. The method of claim 13 further comprising the step of securing the saw guide to the bone prior to the steps of making a cut and cutting to prevent pivotal motion of the saw guide about the pivot pin during those steps.

15. An osteotomy apparatus for positioning and guiding a pair of intersecting planar cuts in a bone, the guide comprising:
   a pivot pin mounted to the bone near the intersection of the two intersecting planar cuts;
   a guide member pivotally coupled to the pivot pin and including a saw guide for establishing a cut plane;
   a cutting device to cut the bone in the cut plane established by the saw guide; and
   an elongate alignment member coupled to the saw guide and extending in an orientation generally transverse to the cut plane, where the alignment member is at least half as long as the bone along their respective elongate axes.

16. The osteotomy apparatus of claim 15 further comprising a profile template coupled to the alignment member to move back and forth along the elongate axis thereof.

17. The osteotomy apparatus of claim 15 wherein the guide member includes a handle disposed on the opposite side of the pivot pin from the saw guide, wherein the saw guide is formed by two elongate fingers separated by a planar slot and wherein the cutting device is a saw blade adapted to fit in the planar slot.

18. The osteotomy apparatus of claim 17 further including a locking member where the alignment member is pivotally connected to the guide member for pivotal motion relative thereto and the locking member selectively locks and releases the pivotal orientation of the alignment member relative to the guide member.

19. The osteotomy apparatus of claim 15 wherein the guide member includes a pivot end disposed opposite the saw guide and where a pivot hole is formed in the pivot end to fit over the pivot pin to pivotally couple the guide member to the pivot pin.

20. The osteotomy apparatus of claim 19 further including a removable pivot shim to be disposed within the pivot hole and around the pivot pin allowing the guide member to be more easily mounted on the pin prior to installation of the pivot shim and thereafter remove any play between the pivot hole and the pivot pin.

21. The osteotomy apparatus of claim 19 further comprising an alignment tube, where the alignment tube has a longitudinal axis and is connected to the guide member between the pivot end and the saw guide and is adapted to receive the alignment member which slides back and forth therein along the longitudinal axis of the alignment tube, where the axis of the alignment tube extends substantially transversely to the cut plane established by the saw guide.

22. The osteotomy apparatus of claim 21 where the alignment tube is immovably fixed to the guide member.

23. The osteotomy apparatus of claim 19 wherein the guide member further includes an elongate cross arm connecting the saw guide and the pivot end, the cross arm including at least one locking hole through which a fastener may be installed to secure the guide member to the bone.

* * * * *